United States Patent
Palmaz et al.

(10) Patent No.: US 8,715,335 B2
(45) Date of Patent: May 6, 2014

(54) ENDOLUMINAL IMPLANTABLE STENT-GRAFTS

(75) Inventors: Julio C. Palmaz, Napa, CA (US); Christopher T. Boyle, Flushing, NY (US); Christopher E. Banas, Breckenridge, CO (US); Roger W. Wiseman, Bulverde, TX (US); Denes Marton, San Antonio, TX (US)

(73) Assignee: Advanced Bio Prosthetic Surfaces, Ltd., a wholly owned subsidiary of Palmaz Scientific, Inc., Dallas, TX (US)

( * ) Notice: Subject to any disclaimer, the term of this patent is extended or adjusted under 35 U.S.C. 154(b) by 479 days.

(21) Appl. No.: 12/652,582

(22) Filed: Jan. 5, 2010

(65) Prior Publication Data

US 2010/0191317 A1  Jul. 29, 2010

Related U.S. Application Data

(63) Continuation of application No. 10/289,843, filed on Nov. 6, 2002, now Pat. No. 7,641,680, which is a continuation of application No. 09/532,164, filed on Mar. 20, 2000, now Pat. No. 6,537,310, which is a continuation-in-part of application No. 09/443,929, filed on Nov. 19, 1999, now Pat. No. 6,379,383.

(51) Int. Cl.
*A61F 2/06* (2013.01)

(52) U.S. Cl.
USPC ............ 623/1.15; 623/1.18; 29/521; 216/52; 216/56; 216/102; 72/367.1; 72/368

(58) Field of Classification Search
CPC ............ A61F 2/91; A61F 2/915; A61F 2/92
USPC ............ 623/1.13, 1.1–1.11, 1.15–1.16, 1.18, 623/1.39–1.4, 1.43, 1.46, 1.49; 204/192.1–192.12; 216/37, 56
See application file for complete search history.

(56) References Cited

U.S. PATENT DOCUMENTS

| | | | |
|---|---|---|---|
| 4,510,182 A | 4/1985 | Cornils et al. | 427/162 |
| 4,751,099 A | 6/1988 | Niino et al. | 427/34 |

(Continued)

FOREIGN PATENT DOCUMENTS

| | | | |
|---|---|---|---|
| CA | 2334223 | 11/2008 | A61F 2/06 |
| EP | 0400947 | 12/1990 | C02C 16/00 |

(Continued)

OTHER PUBLICATIONS

Ametek Specialty Metal Products Online, "Sputtering Targets High-Quality Thin Film Materials", www.ametek84.com/fd-sputtering.html, pp. 1-3.

(Continued)

*Primary Examiner* — Darwin Erezo
*Assistant Examiner* — Kendra Obu
(74) *Attorney, Agent, or Firm* — David G. Rosenbaum; J. Peter Paredes; Rosenbaum IP

(57) ABSTRACT

An implantable endoluminal device that is fabricated from materials that present a blood or body fluid and tissue contact surface that has controlled heterogeneities in material constitution. An endoluminal stent-graft and web-stent that is made of an monolithic material deposited into a monolayer and etched into regions of structural members and web regions subtending interstitial regions between the structural members. An endoluminal graft is also provided which is made of a biocompatible metal or metal-like material. The endoluminal stent-graft is characterized by having controlled heterogeneities in the stent material along the blood flow surface of the stent and the method of fabricating the stent using vacuum deposition methods.

12 Claims, 4 Drawing Sheets

(56) References Cited

U.S. PATENT DOCUMENTS

| | | | |
|---|---|---|---|
| 4,846,834 A | 7/1989 | Von Recum et al. ............ 623/11 |
| 5,049,251 A | 9/1991 | Inoue ..................... 204/192.12 |
| 5,061,914 A | 10/1991 | Busch et al. ................. 337/140 |
| 5,084,151 A | 1/1992 | Vallana et al. ........... 204/192.12 |
| 5,133,732 A | 7/1992 | Wiktor ......................... 606/195 |
| 5,133,845 A | 7/1992 | Vallana et al. ........... 204/192.15 |
| 5,158,750 A | 10/1992 | Finicle ......................... 422/102 |
| 5,242,710 A | 9/1993 | Claar et al. ................. 427/248.1 |
| 5,277,933 A | 1/1994 | Claar et al. ................. 427/248.1 |
| 5,329,514 A | 7/1994 | Eguchi et al. ................. 369/126 |
| 5,370,684 A | 12/1994 | Vallana et al. ..................... 623/1 |
| 5,376,463 A | 12/1994 | Bak et al. ..................... 428/547 |
| 5,387,247 A | 2/1995 | Vallana et al. ..................... 623/2 |
| 5,421,955 A | 6/1995 | Lau et al. ......................... 216/48 |
| 5,456,712 A | 10/1995 | Maginot ............................. 623/1 |
| 5,456,713 A | 10/1995 | Chuter ............................... 623/1 |
| 5,477,864 A | 12/1995 | Davidson ...................... 128/772 |
| 5,514,154 A | 5/1996 | Lau et al. ......................... 606/195 |
| 5,522,882 A | 6/1996 | Gaterud et al. ..................... 623/1 |
| 5,540,820 A | 7/1996 | Terakado et al. .......... 204/192.3 |
| 5,545,210 A | 8/1996 | Hess et al. ......................... 623/1 |
| 5,556,414 A | 9/1996 | Turi ................................ 606/198 |
| 5,569,295 A | 10/1996 | Lam ............................... 606/198 |
| 5,591,226 A | 1/1997 | Trerotola et al. .................. 623/1 |
| 5,593,442 A | 1/1997 | Klein ............................... 623/12 |
| 5,603,721 A | 2/1997 | Lau et al. ....................... 606/195 |
| 5,605,714 A | 2/1997 | Dearnaley et al. ........... 427/2.24 |
| 5,607,445 A | 3/1997 | Summers ....................... 606/198 |
| 5,607,463 A | 3/1997 | Schwartz et al. ................. 623/1 |
| 5,609,629 A | 3/1997 | Fearnot et al. ..................... 623/1 |
| 5,628,788 A | 5/1997 | Pinchuk ............................ 623/1 |
| 5,630,840 A | 5/1997 | Mayer ............................... 623/1 |
| 5,647,858 A | 7/1997 | Davidson ...................... 604/264 |
| 5,649,951 A | 7/1997 | Davidson ...................... 606/198 |
| 5,656,036 A | 8/1997 | Palmaz ............................ 623/12 |
| 5,665,115 A | 9/1997 | Cragg ................................ 623/1 |
| 5,683,448 A | 11/1997 | Cragg ................................ 623/1 |
| 5,683,453 A | 11/1997 | Palmaz ............................ 623/1 |
| 5,685,961 A | 11/1997 | Pourrezaei et al. ...... 204/192.15 |
| 5,690,670 A | 11/1997 | Davidson ...................... 606/198 |
| 5,693,084 A | 12/1997 | Chutter ............................. 623/1 |
| 5,695,517 A | 12/1997 | Marin et al. ................... 606/198 |
| 5,702,419 A | 12/1997 | Berry et al. ................... 606/198 |
| 5,723,219 A | 3/1998 | Kolluri et al. .............. 428/411.1 |
| 5,725,573 A | 3/1998 | Dearnaley et al. ................. 623/2 |
| 5,728,158 A | 3/1998 | Lau et al. ......................... 623/12 |
| 5,735,892 A | 4/1998 | Myers et al. ...................... 623/1 |
| 5,735,896 A | 4/1998 | Amon et al. ..................... 623/11 |
| 5,744,515 A | 4/1998 | Clapper ......................... 523/113 |
| 5,755,775 A | 5/1998 | Trerotola et al. .................. 623/1 |
| 5,765,418 A | 6/1998 | Rosenberg ....................... 72/47 |
| 5,769,884 A * | 6/1998 | Solovay ...................... 623/1.13 |
| 5,772,864 A | 6/1998 | Møller et al. ..................... 205/73 |
| 5,776,161 A | 7/1998 | Globerman ................... 606/194 |
| 5,780,807 A | 7/1998 | Saunders ................... 219/121.71 |
| 5,782,908 A | 7/1998 | Cahalan et al. ..................... 623/1 |
| 5,782,910 A | 7/1998 | Davidson ........................... 623/3 |
| 5,788,558 A | 8/1998 | Klein ............................... 451/36 |
| 5,798,042 A | 8/1998 | Chu et al. ...................... 210/490 |
| 5,811,151 A | 9/1998 | Hendriks et al. ............ 427/2.24 |
| 5,824,036 A | 10/1998 | Lauterjung ....................... 623/1 |
| 5,824,045 A | 10/1998 | Alt ..................................... 623/1 |
| 5,824,049 A | 10/1998 | Ragheb et al. ..................... 623/1 |
| 5,824,054 A * | 10/1998 | Khosravi et al. ............ 623/1.44 |
| 5,824,056 A | 10/1998 | Rosenberg ........................ 623/1 |
| 5,824,058 A | 10/1998 | Ravenscroft et al. ............. 623/1 |
| 5,840,009 A | 11/1998 | Fischell et al. ..................... 600/3 |
| 5,843,117 A | 12/1998 | Alt et al. ......................... 606/194 |
| 5,843,164 A | 12/1998 | Frantzen et al. ................... 623/1 |
| 5,843,289 A | 12/1998 | Lee et al. ..................... 204/192.3 |
| 5,849,206 A | 12/1998 | Amon et al. ...................... 216/63 |
| 5,855,600 A | 1/1999 | Alt ..................................... 623/1 |
| 5,855,802 A | 1/1999 | Acciai et al. ..................... 216/8 |
| 5,855,955 A | 1/1999 | Claar et al. ................. 427/248.1 |
| 5,858,556 A * | 1/1999 | Eckert et al. ................... 428/586 |
| 5,866,113 A | 2/1999 | Hendriks et al. ............ 424/78.17 |
| 5,868,782 A | 2/1999 | Frantzen ....................... 606/198 |
| 5,873,904 A | 2/1999 | Ragheb et al. ..................... 623/1 |
| 5,876,432 A | 3/1999 | Lau et al. .......................... 623/1 |
| 5,879,370 A | 3/1999 | Fischell et al. ................. 606/198 |
| 5,891,507 A | 4/1999 | Jayaraman ................... 427/2.25 |
| 5,895,406 A | 4/1999 | Gray et al. ..................... 606/198 |
| 5,897,911 A | 4/1999 | Loeffler ......................... 427/2.25 |
| 5,899,935 A | 5/1999 | Ding ................................. 623/1 |
| 5,902,332 A | 5/1999 | Schatz ............................... 623/1 |
| 5,907,893 A | 6/1999 | Zadno-Azizi et al. ........... 29/6.1 |
| 5,913,896 A | 6/1999 | Boyle et al. ....................... 623/1 |
| 5,919,225 A | 7/1999 | Lau et al. .......................... 623/1 |
| 5,922,020 A * | 7/1999 | Klein et al. ................... 623/1.15 |
| 5,925,063 A | 7/1999 | Khosravi ...................... 606/200 |
| 5,925,075 A | 7/1999 | Myers et al. ...................... 623/1 |
| 5,928,279 A | 7/1999 | Shannon et al. ................... 623/1 |
| 5,932,299 A | 8/1999 | Katoot ............................ 427/508 |
| 5,938,682 A | 8/1999 | Hojeibane et al. ............ 606/198 |
| 5,938,697 A | 8/1999 | Killion et al. ...................... 623/1 |
| 5,945,153 A | 8/1999 | Dearnaley ..................... 427/2.12 |
| 5,951,881 A | 9/1999 | Rogers et al. .................... 216/41 |
| 5,955,588 A | 9/1999 | Tsang et al. ...................... 536/21 |
| 5,962,138 A | 10/1999 | Kolluri et al. .............. 428/411.1 |
| 5,968,091 A | 10/1999 | Pinchuk et al. .................... 623/1 |
| 5,972,018 A | 10/1999 | Israel et al. ................... 606/198 |
| 5,972,027 A | 10/1999 | Johnson ............................ 623/1 |
| 5,972,441 A | 10/1999 | Campbell et al. ............. 428/34.1 |
| 5,984,905 A | 11/1999 | Dearnaley ..................... 604/265 |
| 5,984,963 A * | 11/1999 | Ryan et al. ................... 623/1.11 |
| 6,001,123 A | 12/1999 | Lau ................................... 623/1 |
| 6,004,348 A | 12/1999 | Banas et al. ....................... 623/1 |
| 6,007,573 A * | 12/1999 | Wallace et al. .............. 623/1.11 |
| 6,015,429 A | 1/2000 | Lau et al. .......................... 623/1 |
| 6,019,784 A | 2/2000 | Hines ................................ 623/1 |
| 6,022,370 A | 2/2000 | Tower ............................ 606/194 |
| 6,027,526 A | 2/2000 | Limon et al. ...................... 623/1 |
| 6,033,433 A | 3/2000 | Ehr et al. ........................... 623/1 |
| 6,039,755 A | 3/2000 | Edwin et al. ...................... 623/1 |
| 6,042,597 A | 3/2000 | Kveen et al. .................. 606/198 |
| 6,042,605 A | 3/2000 | Martin et al. ...................... 623/1 |
| 6,056,776 A | 5/2000 | Lau et al. ...................... 623/1.16 |
| 6,059,808 A | 5/2000 | Boussignac et al. .......... 606/191 |
| 6,066,167 A | 5/2000 | Lau et al. .......................... 623/1 |
| 6,066,168 A | 5/2000 | Lau et al. ...................... 623/1.16 |
| 6,066,169 A | 5/2000 | McGuinness ................ 623/1.16 |
| 6,071,305 A | 6/2000 | Brown et al. ...................... 623/1 |
| 6,086,773 A | 7/2000 | Dufresne et al. .................. 216/8 |
| 6,096,175 A * | 8/2000 | Roth ......................... 204/192.15 |
| 6,106,642 A | 8/2000 | DiCarlo et al. ................ 148/563 |
| 6,124,523 A | 9/2000 | Banas et al. ................... 623/1.11 |
| 6,129,756 A | 10/2000 | Kugler et al. ................. 623/1.27 |
| 6,143,022 A | 11/2000 | Shull et al. ................... 623/1.13 |
| 6,149,681 A * | 11/2000 | Houser et al. ................ 623/1.12 |
| 6,152,995 A * | 11/2000 | Edlund ............................... 96/4 |
| 6,156,064 A | 12/2000 | Chouinard ................... 623/1.44 |
| 6,159,239 A | 12/2000 | Greenhalgh .................. 623/1.13 |
| 6,165,209 A | 12/2000 | Patterson et al. .............. 623/1.1 |
| 6,165,211 A | 12/2000 | Thompson ................... 623/1.13 |
| 6,214,039 B1 | 4/2001 | Banas et al. .................. 623/1.13 |
| 6,251,132 B1 | 6/2001 | Ravenscroft et al. ........ 623/1.11 |
| 6,264,684 B1 | 7/2001 | Banas et al. .................. 623/1.13 |
| 6,273,909 B1 * | 8/2001 | Kugler et al. ................. 623/1.13 |
| 6,287,335 B1 | 9/2001 | Drasler et al. ................ 623/1.28 |
| 6,322,585 B1 | 11/2001 | Khosravi et al. .............. 623/1.11 |
| 6,344,053 B1 | 2/2002 | Boneau ........................ 623/1.11 |
| 6,344,054 B1 | 2/2002 | Parodi .......................... 623/1.13 |
| 6,346,119 B1 | 2/2002 | Kuwahara et al. ........... 623/1.13 |
| 6,348,066 B1 | 2/2002 | Pinchuk et al. .............. 623/1.16 |
| 6,352,553 B1 | 3/2002 | van der Burg et al. ....... 623/1.23 |
| 6,355,058 B1 | 3/2002 | Pacetti et al. ................. 623/1.15 |
| 6,361,637 B2 | 3/2002 | Martin et al. .................. 156/187 |
| 6,383,214 B1 | 5/2002 | Banas et al. .................. 623/1.14 |
| 6,391,052 B2 | 5/2002 | Buirge et al. ................. 623/1.47 |
| 6,398,802 B1 | 6/2002 | Yee ............................... 623/1.13 |
| 6,416,535 B1 | 7/2002 | Lazarus ........................ 623/1.11 |
| 6,428,569 B1 | 8/2002 | Brown .......................... 623/1.15 |
| 6,451,047 B2 | 9/2002 | McCrea et al. ............... 623/1.13 |
| 6,475,232 B1 | 11/2002 | Babbs et al. .................. 623/1.13 |

(56) References Cited

U.S. PATENT DOCUMENTS

| | | | |
|---|---|---|---|
| 6,488,701 B1 | 12/2002 | Nolting et al. | 623/1.13 |
| 6,500,203 B1 | 12/2002 | Thompson et al. | 623/1.13 |
| 6,527,919 B1 * | 3/2003 | Roth | 204/192.15 |
| 6,533,905 B2 * | 3/2003 | Johnson et al. | 204/192.15 |
| 6,620,634 B2 * | 9/2003 | Johnson et al. | 438/14 |
| 6,746,890 B2 * | 6/2004 | Gupta et al. | 438/50 |
| 6,790,298 B2 * | 9/2004 | Johnson et al. | 148/561 |
| 2001/0009169 A1 * | 7/2001 | Kajiwara et al. | 148/563 |

FOREIGN PATENT DOCUMENTS

| | | | | |
|---|---|---|---|---|
| EP | 0442303 | | 8/1991 | C23C 16/26 |
| EP | 836839 | A2 * | 4/1998 | |
| EP | 0850604 | | 2/2003 | A61F 2/06 |
| EP | 0815806 | | 3/2004 | A61F 2/06 |
| JP | 51055724 | | 5/1976 | |
| JP | H06-188135 | | 5/1986 | G01N 27/30 |
| JP | H08-500392 | | 1/1996 | A01N 59/16 |
| JP | H08-126704 | | 5/1996 | A61M 29/02 |
| JP | H08-196642 | | 8/1996 | A61M 29/00 |
| JP | H10-295823 | | 11/1998 | A61M 29/00 |
| JP | H10-295824 | | 11/1998 | A61M 29/00 |
| JP | H11-137694 | | 5/1999 | A61M 29/02 |
| JP | H11-267462 | | 10/1999 | B01D 59/34 |
| WO | WO 97-07257 | | 2/1997 | C23C 14/00 |
| WO | WO 97-44692 | | 11/1997 | G02B 6/16 |
| WO | WO 98-13537 | | 4/1998 | C25D 1/00 |
| WO | WO 98-45506 | | 10/1998 | C25D 7/04 |
| WO | WO 99-23977 | | 5/1999 | A61F 2/06 |
| WO | WO 99-36276 | | 7/1999 | B44C 1/22 |
| WO | WO 99-39765 | | 8/1999 | |
| WO | WO 99-62432 | | 12/1999 | A61F 2/06 |
| WO | WO 00-04204 | | 1/2000 | C23C 14/34 |
| WO | WO 01-53559 | | 7/2001 | A61F 2/06 |
| WO | WO 01-55473 | | 8/2001 | C23C 14/00 |
| WO | WO 01-56502 | | 8/2001 | A61F 2/06 |

OTHER PUBLICATIONS

AVS 46th International Symposium, Paper BI-WeM5, "Biocompatibility of Cardiac Cells on Silane-Modified Surfaces", (Oct. 27, 1999).
AVS 46th International Symposium, Paper BI-WeM7, "Biofunctionalization of Surfaces with Peptide Amphilphiles", (Oct. 27, 1999).
AVS 46th International Symposium, Paper BI-WeM9, "Plasma Copolymer Surfaces for Cell Culture", (Oct. 27, 1999).
AVS 46th International Symposium, Paper BI-FrM2, "Plasma Copolymer Surfaces for the Controlled Adsorption of Common Proteins", (Oct. 29, 1999).
AVS 46th International Symposium, Paper BI-FrM10, "Biofilm—Titanium Chemistry of Adhesion using X-ray Photoelectron Spectroscopy", (Oct. 29, 1999).
AVS 46th International Symposium, Paper BI-FrM10, "Nanoscale Patterning of Gold for Attachment of Supported Lipid Bilayers", (Oct. 29, 1999).
Buchaillot, L., et al., "Constitutive Parts of a Shape Memory Alloy Titanium-Nickel Thin Film Catheter," *Proceedings of the Second International Conference on Shape Memory and Superelastic Technologies Asilomar Conference Center*Pacific Grove, California, USA, pp. 183-188, (1997).
Busch, J.D., et al., "Shape Memory Properties in Ni-Ti Sputter-Deposited Film," *J Appl. Phys*, vol. 68, No. 12, pp. 6224-6226, (Dec. 15, 1990).
Cejna, Manfred, et al., "Primary Implantation of Polyester-Covered Stent-Grafts for Transjugular Intrahepatic Portosystemic Stent Shunts (TIPSS): A Pilot Study," *Cardiovasc Intervent Radiol*, vol. 2, pp. 305-310, (1999).
Curtis, et al., "Reactions of Biological Cells to Nanostructures," AVS 46th International Symposium, Paper BI-WeM2, (Oct. 27, 1999).
Davies, P.F., et al., "Endothelial Cell Adhesion in Real Time. Measurements In Vitro by Tandem Scanning Confocal Image Analysis," *J. Clin Invest*, vol. 91, No. 6, pp. 2640-2652, (Jun. 1991).

Davies, P.F., et al., "Quantitative Studies of Endothelial Cell Adhesion. Directional Remoldeling of Focal Adhesion Sites in Response to Flow Forces," *J. Clin Invest.*, vol. 93, No. 5, pp. 2031-2038, (May 1994).
Daw, R., et al., "Endothelial Cell Organization on Micropatterned Protein Surfaces," AVS 47th International Symposium, Paper No. BI-WeP21, (Oct. 4, 2000).
Ensinger, W., "The Influence of Ion Irradiation During Film Growth on the Chemical Stability of Film/Substrate Systems," *Surface and Coatings Technology*, vol. 80, pp. 35-48. (1996).
Fancey, K.S., et al., (Abstract) "Relative Importance of Bombardment Energy and Intensity in Ion Plating," *Journal of VacuumScience & Technology A: Vacuum, Surfaces and Films*, vol. 13, No. 2, pp. 428-435 (Abstract view), (Mar. 1995).
Gisser, K., et al., (Abstract) "Oriented Nickel-Titanium Shape Memory Alloy Films Prepared by Annealing During Deposition", *Applied Physics Letters*, vol. 61, No. 14, pp. 1632-1634.
Goldberg, F., et al., "The Effects of Ion Irradiation on NiTi Shape Memory Alloy Thin Films," *Proceedings of the Second International Conference on Shape Memory and Superelastic Technologies Asilomar Conference Center*, Pacific Grove, California, USA, pp. 177-182, (1997).
Gordon, et al., (Abstract): "Liquid Sources for Chemical Vapor Deposition of Group 6 Metals and Metal Nitrides,", www.techtransfer.harvard.edu/cgi-bin/TALSearch.cgi?full_report=1&case=3, Case Number 1709.
Gutensohn, Kai, M.D., "Flow Cytometric Investigation", http://www.phytis.com/stent6.htm, pp. 1-3.
Haskal, Z.J., et al., (Abstract): "Porous and Nonporous Polycarbonate Urethane Stent-Grafts for TIPS Formation: Biologic Responses," *J. Vasc. Interv. Radiol*, vol. 10, No. 9, pp. 1255-1263, (Oct. 1999).
Haskal, Z.J., "Improved Patency of Transjugular Intrahepatic Portosystemic Shunts in Humans: Creation and Revision with PTFE stent-grafts[1]'" *Radiology*, vol. 213, No. 3, pp. 759-766, (Dec. 1999).
Houston, J.E., "The Nanomechanical Properties of Thin Films," *AVS 47th International Symposium, Paper No. TF-TuA1*, (Oct. 3, 2000).
IBM, "Multicomponent Film Deposition by Target Biasing," *IBM Technical Disclosure Bulletin*, pp. 1-2, (Jul. 1980).
IEM, "Expertise Concerning the Implementation of the Phytis Diamond As Stent performed at the Institute for Experimental Medicine (IEM)," http://www.phytis.com/stent9.htm, pp. 1.
Inoue, K., et al., "Aortic Arch Reconstruction by Transluminally Placed Endovascular Branched Stent Graft," *Circulation*, pp. II316-II321, (Nov. 9, 1999).
Ishida, A., et al., "Microstructure of Ti-Rich Ti-Ni thin films," *Proceedings of the Second International Conference on Shape Memory and Superelastic Technologies Asilomar Conference Center*, Pacific Grove, California, USA, pp. 161-166, (1997).
Jardine, A. Peter, "Vacuum Conditions for Sputtering Thin Film TiNi," (Abstract view), *Journal of Vacuum Science and Technology, JVST A Online*, pp. 1-2.
Johnson, A.D., et al., "Recent Progress in the Application of Thin Film Shape Memory Alloys," *Proceedings of the First International Conference on Shape Memory and Superelastic Technologies Asilomar Conference Center*, Pacific Grove, California, USA, pp. 299-310, (1994).
Johnson, A.D., et al., "Applications of Shape-Memory Alloy Thin Films," *Proceedings of the Second International Conference on Shape Memory and Superelastic Technologies Asilomar Conference Center*, Pacific Grove, California, USA, pp. 1-12, (1997).
Johnson, et al., "Progress in Thin Film Shape Memory Microactuators," by Johnson, et al., www.sma-mems.com/recent.htm (Overview), pp. 1-5.
Kalman, Peter G., M.D. "Stent-Graft Repair for Abdominal Aortic Aneurysm," *CMAJ*, vol. 161, No. 9, pp. 1133.
Kusano, E., et al., "Anomalous Plastic and Elastic Behaviors of Sputter-Deposited TiNi with 10 or 20 Inserted Thin Al Layers Evaluated by Nanoindentation," *AVS 47th International Symposium, Paper No. Tf-TuA3*, (Oct. 3, 2000).
Mattox, D., "A Concise History of Vacuum Coating Technology, Part 2: 1940 to 1975," www.svc.org/Historyof_Vac2.html, pp. 1-15.

(56) References Cited

OTHER PUBLICATIONS

Mrksich, M., "Model Surfaces for Studying and Controlling the Adhesion of Cells," *AVS 47th International Symposium, Invited Paper No. BI+EL-TuA1*, (Oct. 3, 2000).

Nishikawa, T., et al., "Tissue Formation of Hepatocytes on Micro-Porous Films of Polylactide," *AVS 47th International Symposium, Paper No. BI+EL-TuA10* (Oct. 3, 2000).

Phytis, L.D.A. Home Page Information, http://www.phytis.com/continent/htm, pp. 1-15.

Pingshan, Q., et al., "The Effect of HCD Technological Factors on the NiTi SMA Film Thickness," *Proceedings of the Second International Conference on Shape Memory and Superelastic Technologies Asilomar Conference Center*, Pacific Grove, California, USA, pp. 173-176, (1997).

Quandt, E., et al., "Sputter-Deposition of TiNi, TiNiPd and TiPd Films Displaying the Two-Way Shape-Memory Effect," *Sensors and Actuators*, A53, pp. 434-439, (1996).

Singh, J., "Multilayer Ceramic/Metallic Coatings by Ion Beam-Assisted, Electron Beam Physical Vapor (EB-PVD) Deposition", *Penn State Appled Research Laboratory*, pp. 1-4, (1997).

Stolf, N.A., et al., (Abstract): "Self-Expanding Endovascular Stent-Graft Implant for Treatment of Descending Aortic Diseases", *J. Card. Surg.*, vol. 14, No. 1, pp. 9-15, (Jan.-Feb. 1999).

Sutherland, D.S., et al., "Cell Response to Chemically and Topographically Modified Surfaces," *AVS 47th International Symposium, Paper No. BI+EL-TuA3*, (Oct. 3, 2000).

TiNi Alloy Compay (online), "Thin Film Shape Memory Alloy Microactuators", pp. 1-2.

Uhrmeister, P, et al., (Abstract): "Stents for the Treatment of Aortic Aneurysms. Review of Devices, Technique and Results", *Thromb Haemost*, vol. 82 (Suppl), No. 1, pp. 171-175, (Sep. 1999).

Walker, J.A., et al., "Thin-Film Processing of TiNi Shape Memory Alloy," *Sensors and Actuators*, A21-A23, pp. 243-246, (1990).

Weixin, H., et al., "The Characteristics of NiTi HCD-Deposited SMA Films," *Proceedings of the Second International Conference on Shape Memory and Superelastic Technologies Asilomar Conference Center*, Pacific Grove, California, USA, pp. 167-172, (1997).

Zheng, H., et al., (Abstract): "Clinical Experience with a New Biocompatible Phosphorylcholine-Coated Coronary Stent," *J. Invasive Cardiol*, vol. 11, No. 10, pp. 608-614, (Oct. 1999).

"Adhesion of Bovine Serus Albumin on Coated DLC (Diamond-Like) and Uncoated ($SiO_2$ / $TiO_2$) Sensor Chips," http://wwwphytis.com/stent4.htm, pp. 1-2.

"Amorphous Carbon and C:N. Thin Films," http://www.glue.umd.edu/~astan/avs01.htm.

"Benefits from Diamond-Like Coated Stainless Steel Stents", http://www.phytis.com/stents0.htm, pp. 1-2.

"Directions for Use, Diamond AS® Stent", www.phytis.com/direcuse.htm, pp. 1-8.

"Fabrication of Small-Scale Coils and Bands as Photomasks on Optical Fibers for Generation of In-Fiber Gratings, Electromagnets as Micro-NMR Coils, Microtransformers, and Intra-Vascular Stents," www.techtransfer.harvard.edu/cgi-bin/TALSearch.cgi?full_report=1&case=72, Case Number 1263.

"Focused Ion Beam NonaFabrication," http://www.glue.umd.edu/~astan/avs04.htm.

"Invulnerability and Resistance of DLC-Coating," http://www.phytis.com/stent3.htm, pp. 1-3.

"Material in Use and Its Biocompatibility," http://www.phytis.com/stent5.htm, pp. 1-2.

"Pre-Clinical and Clinical Evaluation," http://www.phytis.com/stent2.htm, pp. 1-2.

"Risk Analysis of Stents with a Diamond-Like Coated Surface for Use in Prosthetic Implants," http://www.phytis.com/risk.htm, pp. 1-6.

"Stents: Literature," http://www.phytis.com/liter.htm, pp. 1-8.

"The New Phytis Stent," http://www.phytis.com/stent1.htm, pp. 1-2.

\* cited by examiner

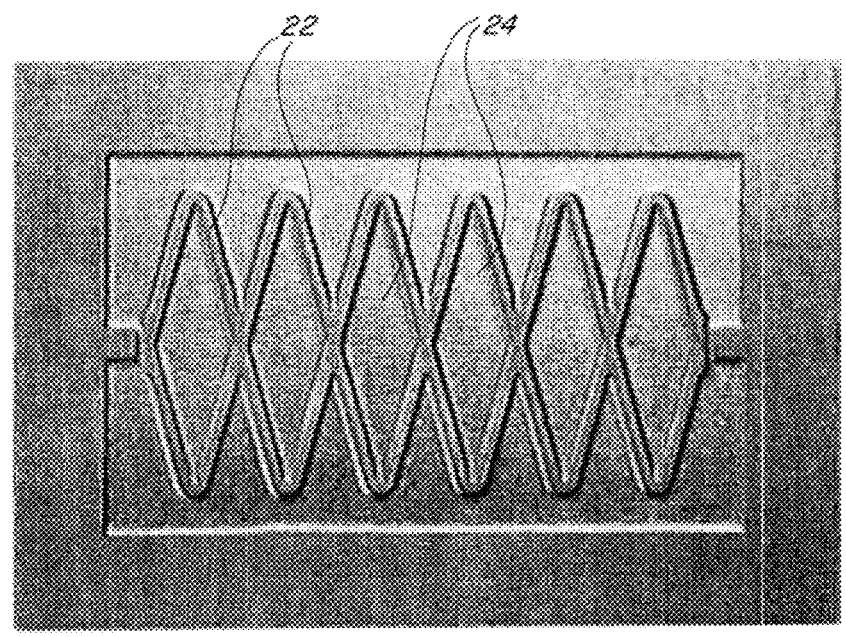
Fig. 1
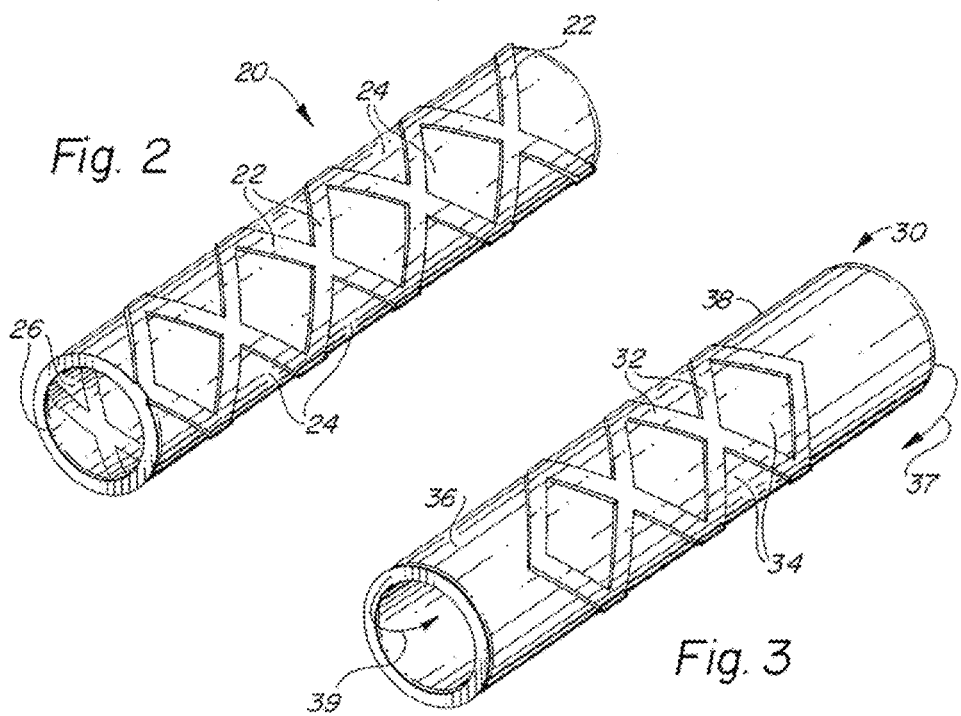
Fig. 2
Fig. 3

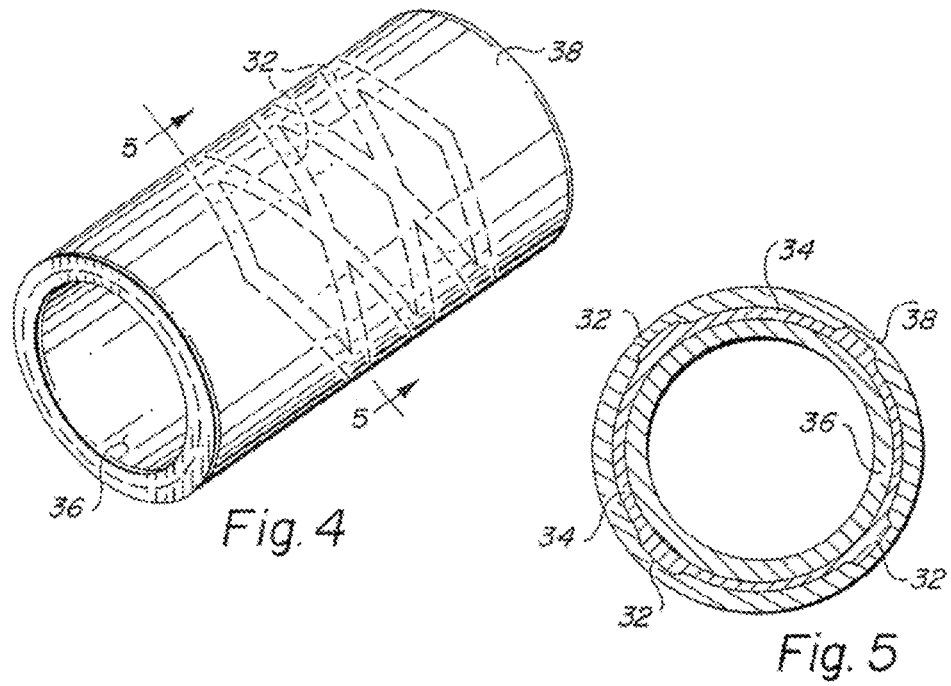
Fig. 4
Fig. 5
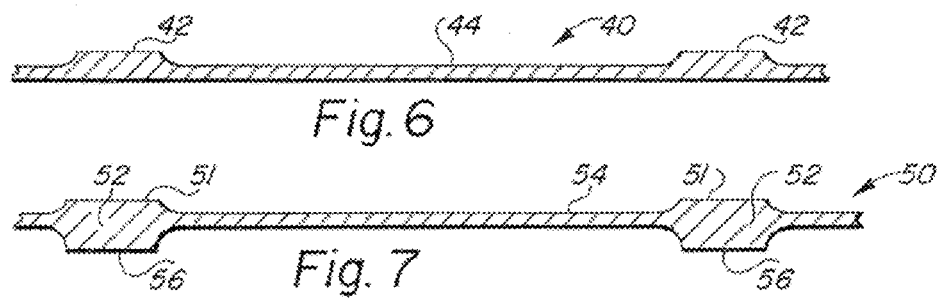
Fig. 6
Fig. 7
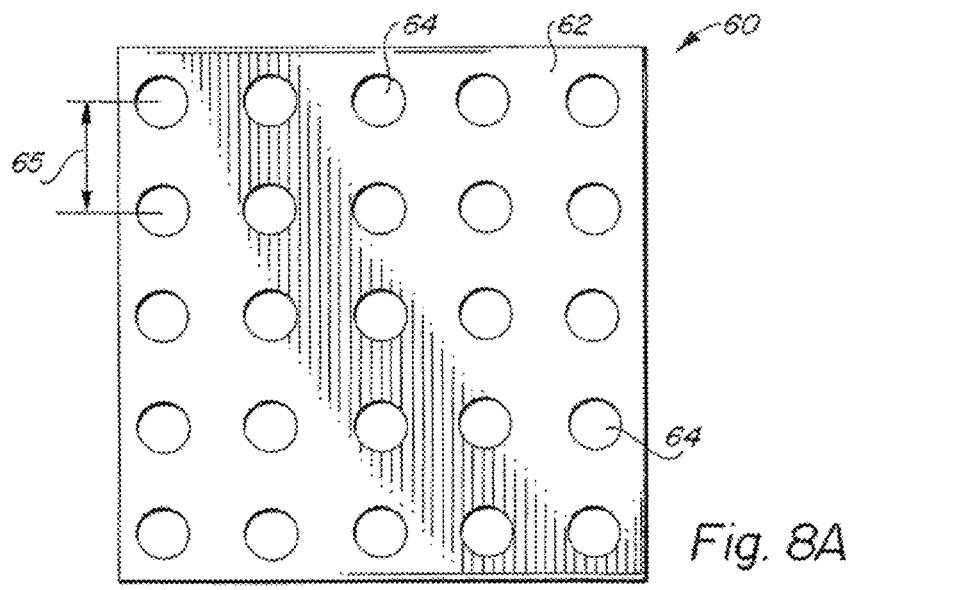
Fig. 8A

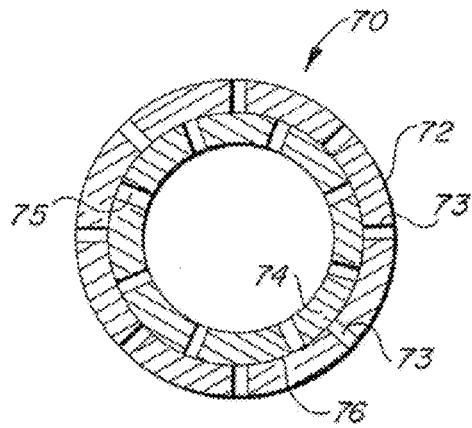
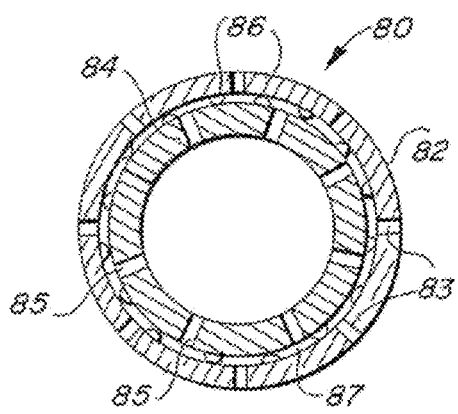
Fig. 9A
Fig. 9B
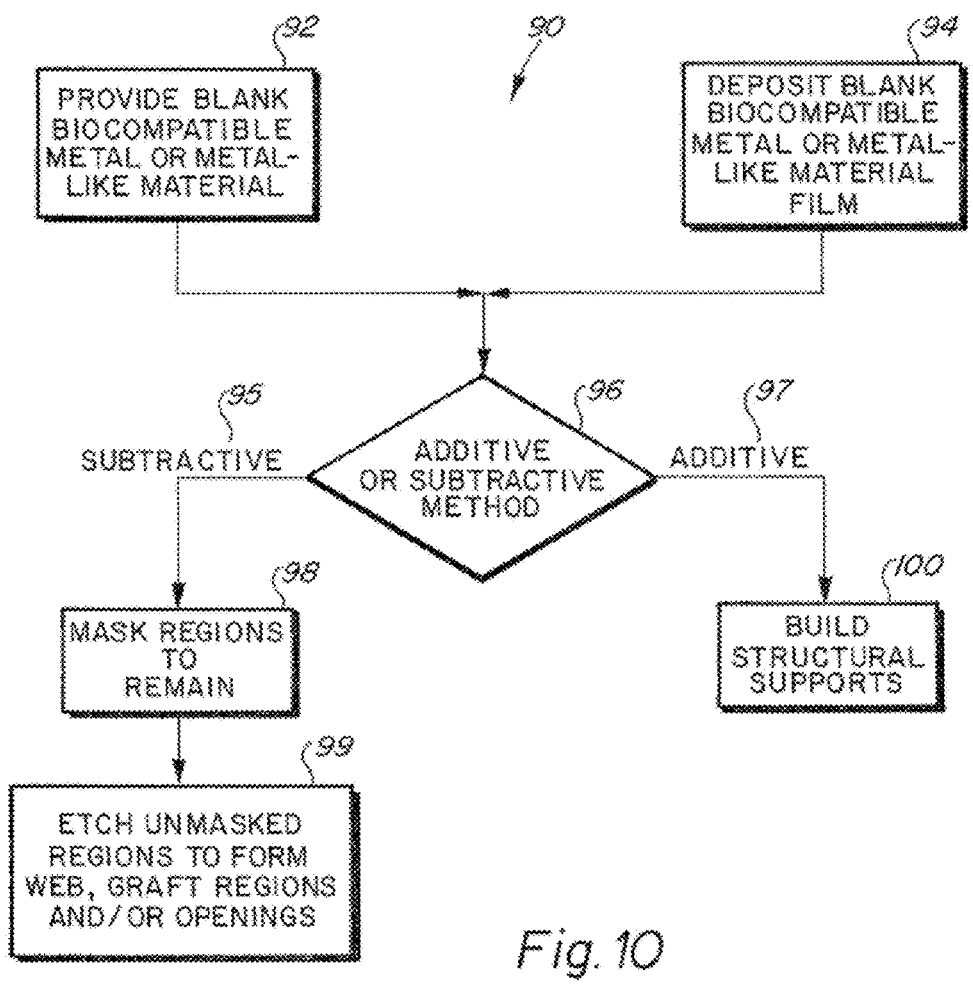
Fig. 10

ENDOLUMINAL IMPLANTABLE STENT-GRAFTS

CROSS REFERENCE TO RELATED APPLICATIONS

The present application is a continuation of application Ser. No. 10/289,843 filed Nov. 6, 2002, now U.S. Pat. No. 7,641,680, issued Jan. 5, 2010 which is a continuation of application Ser. No. 09/532,164 filed Mar. 20, 2000, now U.S. Pat. No. 6,537,310, issued Mar. 25, 2003, and which is a continuation-in-part of application Ser. No. 09/443,929 filed Nov. 19, 1999, now U.S. Pat. No. 6,379,383, issued Apr. 30, 2002, each herein incorporated by reference in their entirety.

BACKGROUND OF THE INVENTION

The present invention pertains generally to implantable medical devices and, more particularly, to implantable medical devices which are capable of being implanted utilizing minimally-invasive delivery techniques. More particularly, the present invention relates to endoluminal grafts, stent-grafts and stent-graft-type devices that are implanted into anatomical passageways using minimally invasive delivery techniques. More specifically, the present invention comprises endoluminal grafts, stent-grafts and stent-graft-type devices that are fabricated entirely of biocompatible metals or of biocompatible materials which exhibit biological response and material characteristics substantially the same as biocompatible metals, such as for example composite materials.

Conventional endoluminal stents and stent-grafts are frequently used post-angioplasty in order to provide a structural support for a blood vessel and reduce the incidence of restenosis following percutaneous balloon angioplasty. A principal example of the present invention are endovascular stents which are introduced to a site of disease or trauma within the body's vasculature from an introductory location remote from the disease or trauma site using an introductory catheter, passed through the vasculature communicating between the remote introductory location and the disease or trauma site, and released from the introductory catheter at the disease or trauma site to maintain patency of the blood vessel at the site of disease or trauma. Stent-grafts are delivered and deployed under similar circumstances and are utilized to maintain patency of an anatomic passageway, for example, by reducing restenosis following angioplasty, or when used to exclude an aneurysm, such as in aortic aneurysm exclusion applications.

While the use of endoluminal stents has successfully decreased the rate of restenosis in angioplasty patients, it has been found that a significant restenosis rate continues to exist even with the use of endoluminal stents. It is generally believed that the post-stenting restenosis rate is due, in major part, to a failure of the endothelial layer to regrow over the stent and the incidence of smooth muscle cell-related neointimal growth on the luminal surfaces of the stent. Injury to the endothelium, the natural nonthrombogenic lining of the arterial lumen, is a significant factor contributing to restenosis at the situs of a stent. Endothelial loss exposes thrombogenic arterial wall proteins, which, along with the generally thrombogenic nature of many prosthetic materials, such as stainless steel, titanium, tantalum, Nitinol, etc. customarily used in manufacturing stents, initiates platelet deposition and activation of the coagulation cascade, which results in thrombus formation, ranging from partial covering of the luminal surface of the stent to an occlusive thrombus. Additionally, endothelial loss at the site of the stent has been implicated in the development of neointimal hyperplasia at the stent situs. Accordingly, rapid re-endothelialization of the arterial wall with concomitant endothelialization of the body fluid or blood contacting surfaces of the implanted device is considered critical for maintaining vasculature patency and preventing low-flow thrombosis.

At present, most endoluminal stents are manufactured of stainless steel, which is known to be thrombogenic. In order to reduce the thrombogenicity of the stainless steel and to maintain sufficient dimensional profiles for catheter delivery, most stents minimize the metal surface area that contacts blood, in order to minimize thrombus formation after implantation. Thus, in order to reduce the thrombogenic response to stent implantation, as well as reduce the formation of neointimal hyperplasia, it would be advantageous to increase the rate at which endothelial cells form endothelium proximal and distal to the stent situs, migrate onto and provide endothelial coverage of the luminal surface of the stent which is in contact with blood flow through the vasculature.

Stent-grafts are essentially endoluminal stents with a discrete covering on either or both of the luminal and abluminal surfaces of the stent that occludes the open spaces, or interstices, between adjacent structural members of the endoluminal stent. It is known in the art to fabricate stent-grafts by covering the stent with endogenous vein or a synthetic material, such as woven polyester known as DACRON, or with expanded polytetrafluoroethylene. Additionally, it is known in the art to cover the stent with a biological material, such as a xenograft or collagen. A primary purpose for covering stents with grafts is to reduce the thrombogenic effect of the stent material. However, conventional grafts are not a complete solution to enhancing the healing response of the devices.

Heretofore, the art has not provided 1) a graft fabricated of biocompatible metals or of biocompatible materials which exhibit in vivo biological and mechanical responses substantially the same as biocompatible metals (hereinafter referred to as "metal-like materials"); 2) a stent-graft device in which a structural component, or stent, and a graft component are each fabricated of metal or metal-like materials; and 3) a stent-graft-type device in which a structural support, such as a stent, defines openings which are subtended by a web, with both the stent and the web being formed as a single, integral, monolithic structure and fabricated of metals or of metal-like materials, this particular embodiment is hereinafter referred to as a "web-stent."

SUMMARY OF THE INVENTION

Graft Embodiment

As used herein the term "Graft" is intended to indicate any type of tubular member which exhibits integral columnar and circumferential strength and which has openings which pass through the thickness of the tubular member.

In accordance with a preferred embodiment of the invention, a graft member is formed as a discrete thin sheet or tube of biocompatible metals or metal-like material. A plurality of openings is provided which pass transversely through the graft member. The plurality of openings may be random or may be patterned. It is preferable that the size of each of the plurality of openings be such as to permit cellular migration through each opening, without permitting fluid flow there through. In this manner, blood cannot flow through the plurality of openings, but various cells or proteins may freely pass through the plurality of openings to promote graft healing in vivo. In accordance with another aspect of the inventive graft embodiment, it is contemplated that two graft members are employed, with an outer diameter of a first graft member being smaller than the inner diameter of a second graft member, such that the first graft member is concentrically engageable within a lumen of the second graft member. Both the first and second graft members have a pattern of a plurality of openings passing there through. The first and second graft members are positioned concentrically with respect to one another, with the plurality of patterned openings being positioned out of phase relative to one another such as to create a tortuous cellular migration pathway through the wall of the concentrically engaged first and second graft members. In order to facilitate cellular migration through and healing of the first and second graft members in vivo, it is preferable to provide additional cellular migration pathways that communicate between the plurality of openings in the first and second graft members. These additional cellular migration pathways may be imparted as 1) a plurality of projections formed on either the luminal surface of the second graft or the abluminal surface of the first graft, or both, which serve as spacers and act to maintain an annular opening between the first and second graft members that permits cellular migration and cellular communication between the plurality of openings in the first and second graft members, or 2) a plurality of microgrooves, which may be random, radial, helical, or longitudinal relative to the longitudinal axis of the first and second graft members, the plurality of microgrooves being of a sufficient size to permit cellular migration and propagation along the groove without permitting fluid flow there through, the microgrooves serve as cellular migration conduits between the plurality of openings in the first and second graft members.

Stent-Graft Embodiment

In accordance with another preferred embodiment of the present invention, a graft member may be formed as either a thin sheet of material or as a tubular member, and mechanically joined to cover a plurality of structural support members. The graft member may be used to cover either a luminal or abluminal surface, or both, of an endoluminal device.

A stent-graft in accordance with the present invention may be formed by conjoining a discrete graft member with a plurality of structural support members, such as a stent, by mechanically joining the graft member to regions of the plurality of structural support members. Alternatively, a stent-graft may be formed by first forming, such as by vacuum deposition methods or by etching a pre-existing material blank, a graft member as a contiguous thin sheet or tube which projects outwardly from at least one aspect of the plurality of structural members. The thin sheet is then everted over the structural members and brought into a position adjacent a terminal portion of the plurality of structural members such that it covers one or both of the putative luminal or abluminal surfaces of the plurality of structural members. The graft member is then mechanically joined at an opposing end, i.e., the putative proximal or the putative distal end of the plurality of structural members.

The stent-graft is formed entirely of a metal or metal-like material, which, as opposed to using conventional synthetic polymeric graft materials, the inventive graft material exhibits improved healing response.

Web-Stent Embodiment

In accordance with one of the embodiments of the present invention, there is provided a stent-graft-type device, termed a "web-stent" in which there is at least one of a plurality of structural members that provide a primary means of structural support for the webbed-stent device. The plurality of structural members may be arranged in any manner as is known in the art of stent fabrication, e.g., single element forming a circle or ellipse, a single or plural elements which form a tubular diamond-like or undulating pattern, in which adjacent structural members are spaced apart forming open regions or interstices between adjacent structural members. In the present invention, the interstices or open regions between adjacent structural members are subtended by a web of material that is the same material or a material exhibiting similar biological and mechanical response as the material that forms the plurality of structural members. The web may be formed within all or a portion of the interstitial area or open regions between the plurality of structural support members.

Method of Making Graft, Stent-Graft and Web-Stent

Finally, the present invention provides a method of fabricating the graft, stent-graft and web-stent devices of the present invention. The inventive method consists of forming the device by vacuum deposition of a film, either as a planar sheet or as a tube, of a biocompatible material, such as nickel-titanium alloys. The thickness of the deposited material is determined by the particular embodiment being fabricated. After the deposited film is created, either additive or subtractive methodologies are employed to define: the structural members, the interstitial web regions, the graft regions and/or a plurality of openings through the deposited film. Alternatively, a pre-fabricated starting film of a biocompatible material, such as Nitinol, may be employed, and the stent-pattern formed by vacuum deposition methods or by conventional metal forming techniques, or by removing regions of the pre-fabricated film to form the interstitial regions of the web-stent device.

Where a graft member is being fabricated, the thickness of the deposited or pre-fabricated starting film may be less than that where a web-stent is being formed, due to the absence of structural members in the graft member. However, where a stent-graft or a web-stent is being fabricated, structural members may be formed by alternative methods. The structural members may be formed by additive techniques by applying a pattern of structural members onto a film, such as by vacuum deposition techniques or conventional metal forming techniques, such as laminating or casting. Second, subtractive or selective removal techniques may be employed to remove material from patterned regions on a film, such as by etching a pattern of interstitial regions between adjacent structural members until a thinner film is created which forms the web subtending the plurality of structural members. Where a pre-existing stent is employed as the structural members, obviously, the structural members do not need to be fabricated or formed.

In accordance with the best mode contemplated for the present invention, the graft, the plurality of structural members and the web are fabricated of the same or similar metals or metal-like materials. In order to improve healing response, it is preferable that the materials employed have substantially homogenous surface profiles at the blood or tissue contact surfaces thereof. A substantially homogeneous surface profile is achieved by controlling heterogeneities along the blood or tissue-contacting surface of the material. The heterogeneities that are controlled in accordance with an embodiment of the present invention include: grain size, grain phase, grain material composition, stent-material composition, and surface topography at the blood flow surface of the stent. Additionally, the present invention provides methods of making endoluminal devices having controlled heterogeneities in the device material along the blood flow or tissue-contacting surface of the device. Material heterogeneities are preferably controlled by using conventional methods of vacuum deposition of materials onto a substrate.

The surface of a solid, homogeneous material can be conceptualized as having unsaturated inter-atomic and intermolecular bonds forming a reactive plane ready to interact with the environment. In practice, a perfectly clean surface is unattainable because of immediate adsorption of airborne species, upon exposure to ambient air, of O, $O_2$, $CO_2$, $SO_2$, NO, hydrocarbons and other more complex reactive molecules. Reaction with oxygen implies the formation of oxides on a metal surface, a self-limiting process, known as passivation. An oxidized surface is also reactive with air, by adsorbing simple, organic airborne compounds. Assuming the existence of bulk material of homogeneous subsurface and surface composition, oxygen and hydrocarbons may adsorb homogeneously. Therefore, further exposure to another environment, such as the vascular compartment, may be followed by a uniform biological response.

Current metallic vascular devices, such as stents, are made from bulk metals made by conventional methods, and stent precursors, such as hypotubes, are made by many steps that introduce processing aides to the metals. For example, olefins trapped by cold drawing and transformed into carbides or elemental carbon deposit by heat treatment, typically yield large carbon rich areas in 316L stainless steel tubing manufactured by cold drawing process. The conventional stents have marked surface and subsurface heterogeneity resulting from manufacturing processes (friction material transfer from tooling, inclusion of lubricants, chemical segregation from heat treatments). This results in formation of surface and subsurface inclusions with chemical composition and, therefore, reactivity different from the bulk material. Oxidation, organic contamination, water and electrolytic interaction, protein adsorption and cellular interaction may, therefore, be altered on the surface of such inclusion spots. Unpredictable distribution of inclusions such as those mentioned above provide an unpredictable and uncontrolled heterogeneous surface available for interaction with plasma proteins and cells. Specifically, these inclusions interrupt the regular distribution pattern of surface free energy and electrostatic charges on the metal surface that determine the nature and extent of plasma protein interaction. Plasma proteins deposit nonspecifically on surfaces according to their relative affinity for polar or non-polar areas and their concentration in blood. A replacement process known as the Vroman effect, Vroman L., *The importance of surfaces in contact phase reactions, Seminars of Thrombosis and Hemostasis* 1987; 13(1): 79-85, determines a time-dependent sequential replacement of predominant proteins at an artificial surface, starting with albumin, following with IgG, fibrinogen and ending with high molecular weight kininogen. Despite this variability in surface adsorption specificity, some of the adsorbed proteins have receptors available for cell attachment and therefore constitute adhesive sites. Examples are: fibrinogen glycoprotein receptor IIbIIIa for platelets and fibronectin RGD sequence for many blood activated cells. Since the coverage of an artificial surface with endothelial cells is a favorable endpoint in the healing process, favoring endothelialization in device design is desirable in implantable vascular device manufacturing.

Normally, endothelial cells (EC) migrate and proliferate to cover denuded areas until confluence is achieved. Migration, quantitatively more important than proliferation, proceeds under normal blood flow roughly at a rate of 25 µm/hr or 2.5 times the diameter of an EC, which is nominally 10 µm. EC migrate by a rolling motion of the cell membrane, coordinated by a complex system of intracellular filaments attached to clusters of cell membrane integrin receptors, specifically focal contact points. The integrins within the focal contact sites are expressed according to complex signaling mechanisms and eventually couple to specific amino acid sequences in substrate adhesion molecules (such as RGD, mentioned above). An EC has roughly 16-22% of its cell surface represented by integrin clusters. Davies, P. F., Robotewskyi A., Griem M. L. *Endothelial cell adhesion in real time. J. Clin. Invest.* 1993; 91:2640-2652, Davies, P. F., Robotewski, A., Griem, M. L., *Qualitative studies of endothelial cell adhesion, J. Clin. Invest.* 1994; 93:2031-2038. This is a dynamic process, which implies more than 50% remodeling in 30 minutes. The focal adhesion contacts vary in size and distribution, but 80% of them measure less than 6 µm2, with the majority of them being about 1 $\mu m^2$, and tend to elongate in the direction of flow and concentrate at leading edges of the cell. Although the process of recognition and signaling to determine specific attachment receptor response to attachment sites is incompletely understood, regular availability of attachment sites, more likely than not, would favorably influence attachment and migration. Irregular or unpredictable distribution of attachment sites, that might occur as a result of various inclusions, with spacing equal or smaller to one whole cell length, is likely to determine alternating hostile and favorable attachment conditions along the path of a migrating cell. These conditions may vary from optimal attachment force and migration speed to insufficient holding strength to sustain attachment, resulting in cell slough under arterial flow conditions. Due to present manufacturing processes, current implantable vascular devices exhibit such variability in surface composition as determined by surface sensitive techniques such as atomic force microscopy, X-ray photoelectron spectroscopy and time-of-flight secondary ion mass spectroscopy.

There have been numerous attempts to increase endothelialization of implanted stents, including covering the stent with a polymeric material (U.S. Pat. No. 5,897,911), imparting a diamond-like carbon coating onto the stent (U.S. Pat. No. 5,725,573), covalently binding hydrophobic moieties to a heparin molecule (U.S. Pat. No. 5,955,588), coating a stent with a layer of blue to black zirconium oxide or zirconium nitride (U.S. Pat. No. 5,649,951), coating a stent with a layer of turbostratic carbon (U.S. Pat. No. 5,387,247), coating the tissue-contacting surface of a stent with a thin layer of a Group VB metal (U.S. Pat. No. 5,607,463), imparting a porous coating of titanium or of a titanium alloy, such as Ti—Nb—Zr alloy, onto the surface of a stent (U.S. Pat. No. 5,690,670), coating the stent, under ultrasonic conditions, with a synthetic or biological, active or inactive agent, such as heparin, endothelium derived growth factor, vascular growth factors, silicone, polyurethane, or polytetrafluoroethylene, U.S. Pat. No. 5,891,507), coating a stent with a silane compound with vinyl functionality, then forming a graft polymer by polymerization with the vinyl groups of the silane compound (U.S. Pat. No. 5,782,908), grafting monomers, oligomers or polymers onto the surface of a stent using infrared radiation, microwave radiation or high voltage polymerization to impart the property of the monomer, oligomer or polymer to the stent (U.S. Pat. No. 5,932,299).

Thus, the problems of thrombogenicity and re-endothelialization associated with stents have been addressed by the art in various manners which cover the stent with either a biologically active or an inactive covering which is less thrombogenic than the stent material and/or which has an increased capacity for promoting re-endothelialization of the stent situs. These solutions, however, all require the use of existing stents as substrates for surface derivatization or modification, and each of the solutions result in a biased or laminate structure built upon the stent substrate. These prior art coated stents are susceptible to delaminating and/or cracking of the coating when mechanical stresses of transluminal catheter delivery and/or radial expansion in vivo. Moreover, because these prior art stents employ coatings applied to stents fabricated in accordance with conventional stent formation techniques, e.g., cold-forming metals, the underlying stent substrate is characterized by uncontrolled heterogeneities on the surface thereof. Thus, coatings merely are laid upon the heterogeneous stent surface, and inherently conform to the topographical heterogeneities in the stent surface and mirror these heterogeneities at the blood contact surface of the resulting coating. This is conceptually similar to adding a coat of fresh paint over an old coating of blistered paint; the fresh coating will conform to the blistering and eventually, blister and delaminate from the underlying substrate. Thus, topographical heterogeneities are typically telegraphed through a surface coating. Chemical heterogeneities, on the other hand, may not be telegraphed through a surface coating but may be exposed due to cracking or peeling of the adherent layer, depending upon the particular chemical heterogeneity.

The current invention entails creating materials specifically designed for manufacture of grafts, stents, stent-grafts and other endoluminal devices. According to a preferred embodiment of the invention, the manufacture of grafts, stents, stent-grafts and other endoluminal devices is controlled to attain a regular, homogeneous atomic and molecular pattern of distribution along their surface. This avoids the marked variations in surface composition, creating predictable oxidation and organic adsorption patterns and has predictable interactions with water, electrolytes, proteins and cells. Particularly, EC migration is supported by a homogeneous distribution of binding domains that serve as natural or implanted cell attachment sites, in order to promote unimpeded migration and attachment. Based on observed EC attachment mechanisms such binding domains should have a repeating pattern along the blood contact surface of no less than 1 μm radius and 2 μm border-to-border spacing between binding domains. Ideally, the inter-binding domain spacing is less than the nominal diameter of an endothelial cell in order to ensure that at any given time, a portion of an endothelial cell is in proximity to a binding domain.

In accordance with the present invention, there is provided a web-stent device in which there is at least one of a plurality of structural members that provides a primary means of structural support for the web-stent device. The plurality of structural members is spaced apart to form open regions or interstices between adjacent structural members. In the present invention, a web of material, that is the same or similar to the material which forms the plurality of structural members, subtends the interstices or open regions between adjacent structural members. The web may be formed within all or a portion of the interstitial area or open regions between the plurality of structural support members. Both the plurality of interconnected structural members and the web may be formed of initially substantially planar materials or of initially substantially cylindrical materials.

In accordance with another preferred embodiment of the present invention, there is provided a stent-graft device in which a graft member is formed as a film of material and mechanically joined to one or both of the proximal and distal ends of the plurality of structural support members, and covers that surface of the plurality of structural support members which is to form either the luminal or abluminal surface of the stent-graft device. The graft member may be formed either separately or as a contiguous thin-film projecting from the plurality of structural members. Where the graft member is formed as a contiguous thin-film projecting from the plurality of structural members, the thin film is either abluminally everted or luminally inverted and brought into a position adjacent to the plurality of structural members such that it covers either, or both, the luminal or abluminal surfaces or the plurality of structural members, then is attached at an opposing end, i.e., the putative proximal or the putative distal end of the plurality of structural members.

In accordance with another embodiment of the invention, there is provided a graft formed as a discrete thin sheet or tube of biocompatible metal or metal-like materials. A plurality of openings is provided which pass transversely through the graft member. The plurality of openings may be random or may be patterned. It is preferable that the size of each of the plurality of openings be such as to permit cellular migration through each opening, without permitting fluid flow there through. In this manner, blood cannot flow through the plurality of openings, but various cells or proteins may freely pass through the plurality of openings to promote graft healing in vivo.

In accordance with another aspect of the inventive graft embodiment, it is contemplated that two graft members are employed, with an outer diameter of a first graft member being smaller than the an inner diameter of a second graft member, such that the first graft member is concentrically engageable within a lumen of the second graft member. Both the first and second graft members have a plurality of patterned openings passing there through. The first and second graft members are positioned concentrically with respect to one another, with the plurality of patterned openings being positioned out of phase relative to one another such as to create a tortuous cellular migration pathway through the wall of the concentrically engaged first and second graft members. In order to facilitate cellular migration and healing of the first and second graft members, it is preferable to provide additional cellular migration pathways that communicate between the plurality of openings in the first and second graft members. These additional cellular migration pathways may be imparted as 1) a plurality of projections formed on either the luminal surface of the second graft or the abluminal surface of the first graft, or both, which serve as spacers and act to maintain an annular opening between the first and second graft members and permit cellular migration in order to communicate between the plurality of openings in the first and second graft members, or 2) a plurality of microgrooves, which may be random, radial, helical, or longitudinal relative to the longitudinal axis of the first and second graft members, the plurality of microgrooves being of a sufficient size to permit cellular migration and propagation along the groove without permitting fluid flow there through, the microgrooves serve as cellular migration conduits between the plurality of openings in the first and second graft members.

The present invention also provides a method of fabricating the web-stent device which entails providing a planar or tubular film of a biocompatible material, such as forming the film by vacuum deposition, then removing interstitial regions until a thinner film region is created which forms a web subtending a plurality of structural members. Alternatively, a pre-existing conventionally produced sheet or tube of a biocompatible material, such as Nitinol, may be etched until a thinner film is created in the etched regions, thereby forming the interstitial web areas of the web-stent device.

Finally, in accordance with the present invention, there is provided an implantable endoluminal device that is fabricated from materials that present a blood or tissue contact surface that is substantially homogeneous in material constitution.

More particularly, the present invention provides an endoluminal graft, stent, stent-graft and web-stent that is made of a material having controlled heterogeneities along the blood flow or tissue-contacting surface of the stent.

BRIEF DESCRIPTION OF THE FIGURES

FIG. 1 is a photographic top plan view of a web-stent in accordance with the present invention.

FIG. 2 is a perspective view of a preferred embodiment of the web-stent of the present invention.

FIG. 3 is a perspective view of a stent-graft in accordance with the present invention.

FIG. 4 is a perspective view of an alternative embodiment of the inventive stent-graft.

FIG. 5 is a cross-sectional view taken along line 5-5 of FIG. 4.

FIG. 6 is a cross-sectional view illustrating a pair of support members and a section of interstitial web between adjacent supporting members.

FIG. 7 is a cross-sectional view illustrating a pair of support members and a section of interstitial web between adjacent supporting members in accordance with an alternative embodiment of the present invention.

FIG. 8A is a top plan view of a graft or web region with a plurality of openings passing there through.

FIG. 8B is a top plan view of an alternative embodiment of a graft or web region of the present invention with a plurality of openings passing there through.

FIG. 8C is a top plan view of a third embodiment of a graft or web region of the present invention with a plurality of openings passing there through.

FIG. 9A is a transverse cross-sectional view of a first embodiment of a graft member in accordance with the present invention.

FIG. 9B is a transverse cross-sectional view of a second embodiment of a graft member in accordance with the present invention.

FIG. 10 is a flow chart diagrammatically illustrating the method of fabricating the graft, stent-graft and/or web-stent of the present invention.

DETAILED DESCRIPTION OF THE PREFERRED EMBODIMENTS

Figure 8B:
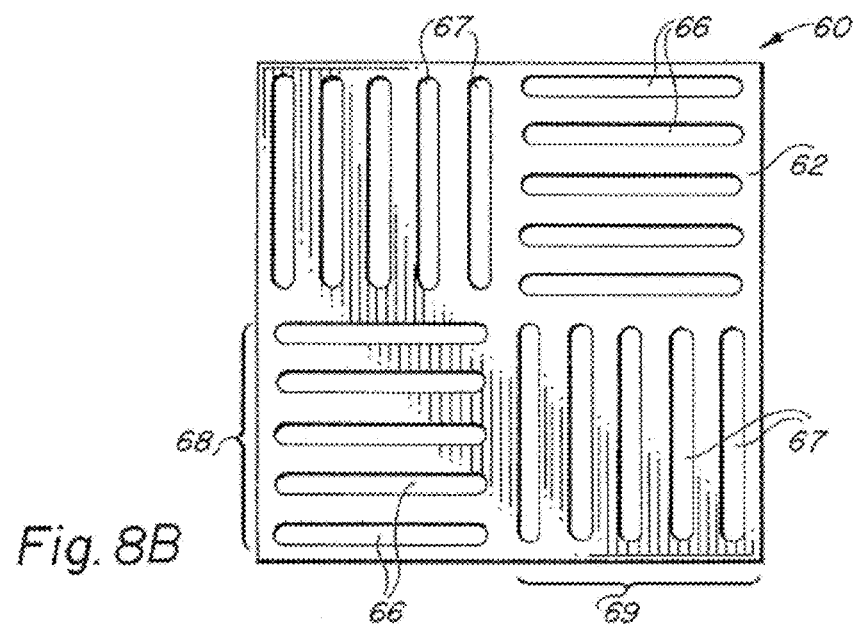

According to the present invention, stent, web-stent and stent-graft devices are provided which preferably exhibit substantially homogenous surface properties. The inventive graft, stent, stent-graft and web-stent devices may be made utilizing a pre-fabricated film or a deposited film, either in a planar or cylindrical conformation, then either adding a pattern of support members to the film or removing at least some regions of the film to create thinner regions in the starting film and defining relatively thinner and thicker film regions, such as thinner web regions between adjacent structural members formed by thicker film regions and/or relatively thinner graft regions. An additive methodology may include vacuum deposition or lamination of a pattern of support members upon the planar or cylindrical film. A subtractive methodology includes etching unwanted regions of material by masking regions to form the structural members and expose unmasked regions to the etchant. Additionally, in order to improve in vivo healing, it is advantageous to impart openings passing through the web or the graft. The openings are preferably produced during the process of forming the web or the graft. The openings in the web or the graft may be formed by conventional methods such as photolithographic processes, by masking and etching techniques, by mechanical means, such as laser ablation, EDM, or micromachining, etc. Suitable deposition methodologies, as are known in the microelectronic and vacuum coating fabrication arts and incorporated herein by reference, are plasma deposition and physical vapor deposition which are utilized to impart a metal layer onto the stent pattern.

In accordance with an aspect of the present invention there is provided a vacuum deposited device that is fabricated of a material having substantially homogeneous surface properties across the blood contact surface of the device. Current manufacturing methods for fabricating endoluminal stents fail to achieve the desired material properties of the present invention. As discussed above, stents are fabricated from bulk metals that are processed in a manner that incorporates processing aides to the base metal. Presently, stents are made from hypotubes formed from bulk metals, by machining a series of slots or patterns into the hyptotube to accommodate radial expansion, or by weaving wires into a mesh pattern.

The present invention consists of a stent made of a bulk material having controlled heterogeneities on the luminal surface thereof. Heterogeneities are controlled by fabricating the bulk material of the stent to have defined grain sizes that yield areas or sites along the surface of the stent having optimal protein binding capability. The characteristically desirable properties of the inventive stent are: (a) optimum mechanical properties consistent with or exceeding regulatory approval criteria, (b) controlling discontinuities, such as cracking or pinholes, (c) a fatigue life of 400 MM cycles as measured by simulated accelerated testing, (d) corrosion resistance, (e) biocompatibility without having biologically significant impurities in the material, (f) a substantially non-frictional abluminal surface to facilitate atraumatic vascular crossing and tracking and compatible with transcatheter techniques for stent introduction, (g) radiopaque at selected sites and MRI compatible, (h) have a luminal surface which is optimized for surface energy and microtopography, (i) minimal manufacturing and material cost consistent with achieving the desired material properties, and (j) high process yields.

Controlling the surface profile of an endoluminal device is significant because blood protein interactions with surfaces of endoluminal devices appear to be the initial step in a chain of events leading to tissue incorporation of the endovascular device. The present invention is based, in part, upon the relationship between surface energy of the material used to make the endoluminal device and protein adsorption at the surface of the endoluminal device. The present inventors have found that a relationship exists between surface free energy and protein adsorption on metals commonly used in fabrication of endoluminal devices. In addition, specific electrostatic forces resident on the surface of metal endoluminal stents have been found to influence blood interactions with the stent surface and the vascular wall.

In accordance with a preferred embodiment the present invention, the inventive grafts, stent-grafts and web-stents have surface profiles which are achieved by fabricating the graft, stent-graft and web-stent by the same metal deposition methodologies as are used and standard in the microelectronic and nano-fabrication vacuum coating arts, and which are hereby incorporated by reference. In accordance with a preferred embodiment the present invention, the preferred deposition methodologies include ion-beam assisted evaporative deposition and sputtering techniques. In ion beam-assisted evaporative deposition it is preferable to employ dual and simultaneous thermal electron beam evaporation with simultaneous ion bombardment of the material being deposited using an inert gas, such as argon, xenon, nitrogen or neon. Bombardment with inert gas ions during deposition serves to reduce void content by increasing the atomic packing density in the deposited material. The reduced void content in the deposited material allows the mechanical properties of that deposited material to be similar to the bulk material properties. Deposition rates up to 20 nm/sec are achievable using ion beam-assisted evaporative deposition techniques.

When sputtering techniques are employed, a 200-micron thick stainless steel film may be deposited within about four hours of deposition time. With the sputtering technique, it is preferable to employ a cylindrical sputtering target, a single circumferential source that concentrically surrounds the substrate that is held in a coaxial position within the source.

Alternate deposition processes which may be employed to form the stent in accordance with the present invention are cathodic arc, laser ablation, and direct ion beam deposition. As known in the metal fabrication arts, the crystalline structure of the deposited film affects the mechanical properties of the deposited film. These mechanical properties of the deposited film may be modified by post-process treatment, such as by, for example, annealing.

Materials to make the inventive graft, stent-graft and web-stent are chosen for their biocompatibility, mechanical properties, i.e., tensile strength, yield strength, and their ease of deposition include, without limitation, the following: elemental titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel.

During deposition, the chamber pressure, the deposition pressure and the partial pressure of the process gases are controlled to optimize deposition of the desired species onto the substrate. As is known in the microelectronic fabrication, nano-fabrication and vacuum coating arts, both the reactive and non-reactive gases are controlled and the inert or non-reactive gaseous species introduced into the deposition chamber are typically argon and nitrogen. The substrate may be either stationary or moveable; either rotated about its longitudinal axis, moved in an X-Y plane, planatarily or rotationally moved within the deposition chamber to facilitate deposition or patterning of the deposited material onto the substrate. The deposited material maybe deposited either as a uniform solid film onto the substrate, or patterned by (a) imparting either a positive or negative pattern onto the substrate, such as by etching or photolithography techniques applied to the substrate surface to create a positive or negative image of the desired pattern or (b) using a mask or set of masks which are either stationary or moveable relative to the substrate to define the pattern applied to the substrate. Patterning may be employed to achieve complex finished geometries of the resultant structural supports, web-regions or graft, both in the context of spatial orientation of patterns of regions of relative thickness and thinness, such as by varying the thickness of the film over its length to impart different mechanical characteristics under different delivery, deployment or in vivo environmental conditions.

The device may be removed from the substrate after device formation by any of a variety of methods. For example, the substrate may be removed by chemical means, such as etching or dissolution, by ablation, by machining or by ultrasonic energy. Alternatively, a sacrificial layer of a material, such as carbon, aluminum or organic based materials, such as photoresists, may be deposited intermediate the substrate and the stent and the sacrificial layer removed by melting, chemical means, ablation, machining or other suitable means to free the stent from the substrate.

The resulting device may then be subjected to post-deposition processing to modify the crystalline structure, such as by annealing, or to modify the surface topography, such as by etching to expose a heterogeneous surface of the device.

Turning now to the Figures, there is illustrated alternative preferred embodiments of the present invention. In FIGS. 1 and 2 there is illustrated a web-stent 20 in accordance with the present invention. The web-stent 20 is formed of a material blank 10, which has been either pre-manufactured or has been vacuum deposited as a planar or cylindrical film. The web-stent 20 is formed by masking regions of the material blank which are to form a plurality of structural members 22, and then etching the unmasked regions which then form interstitial webs 24 which subtend interstitial regions between adjacent structural members 22. The interstitial webs 24 are etched to a material thickness that is less than the thickness of the plurality of structural members 22. It is preferable to impart a plurality of openings in the interstitial webs 24 in order to permit endothelialization of the luminal surface 26 of the interstitial webs 24. The openings may be imparted as a random pattern or as a regular pattern in the interstitial web 24, as will be discussed hereinafter.

With reference to FIG. 3 there is depicted a stent-graft 30 in accordance with the present invention. Stent-graft 30 is formed either from a tubular or planar material blank, which is etched to form the plurality of structural members 32 and interstitial regions 34 between the structural members 32. In addition, either or both a proximal 36 or a distal 38 graft region of the stent are provided and project outwardly from terminal structural members 32. The proximal graft region 36 and the distal graft region 38 are preferably etched to a reduced thickness of less than the thickness of the structural members, and are made with openings passing there through which promote cellular migration, as will be discussed hereinafter.

Under certain applications it may be useful to employ the stent-graft 30 with either or both of the proximal 36 or distal 38 graft regions projecting outwardly from the structural supports 32. An alternative embodiment of the invention is illustrated in FIGS. 4 and 5. The alternative embodiment of the stent-graft 30 involves covering the luminal and abluminal surfaces of a plurality of structural supports 32 with a luminal graft 36 and an abluminal graft 38. The luminal graft 36 may initially be formed as the proximal graft region 36 in FIG. 3 and be luminally inverted 39 and passed into the lumen defined by the structural members 32. The abluminal graft 38 may initially be formed as the distal graft region 38 in FIG. 3 and be abluminally everted 37 over the structural members 32. Alternatively, the luminal graft 36 and the abluminal graft 38 may be formed as either pre-fabricated discrete graft members made of biocompatible metal or metal-like materials that are either tubular or planar then formed into a tube and concentrically engaged about the plurality of structural members 32. Portions of each of the abluminal graft 38 and the luminal graft 36 are mechanically joined to the plurality of structural members 32 or to one and other, thereby effectively encapsulating the plurality of structural members 32 between the luminal graft 36 and the abluminal graft 38. It is preferable that opposing free ends of each of the abluminal graft 38 and luminal graft 36 are mechanically joined to and co-terminus with a terminal portion of the plurality of structural members 32. Mechanical joining may be accomplished by methods such as welding, suturing, adhesive bonding, soldering, thermobonding, riveting, crimping, or dovetailing. In accordance with an alternate embodiment of the invention, the interstitial regions 34 may be subtended by a web 34, as discussed hereinabove, with reference to FIGS. 1 and 2.

Those of ordinary skill in the art, will understand and appreciate that alternative methods of removing material from areas that form relatively thinner regions of the stent, web-stent or stent-graft may be employed. For example, in addition to chemical etching, relatively thinner regions may be formed by removing bulk material by ion milling, laser ablation, EDM, laser machine, electron beam lithography, reactive ion etching, sputtering or equivalent methods which are capable of reducing the thickness of the material in either the graft region or the interstitial web region between the structural members. Alternatively, the structural members may be added to the defined interstitial web or graft regions to form the device, or the interstitial web or graft regions may be added to pre-existing structural members. Additive methods that may be employed include conventional metal forming techniques, including laminating, plating, or casting.

Similarly, a wide variety of initial bulk material configurations may be employed, including a substantially planar sheet substrate, an arcuate substrate or a tubular substrate, which is then processed by either subtractive or additive techniques discussed above.

By forming the structural members, the interstitial web and/or the graft of an integral, monolithic material, both the circumferential or hoop strength of the resultant device, as well as the longitudinal or columnar strength of the device are enhanced over conventional stent-graft devices. Additional advantages of the present invention, depending upon fabrication methods, may include: controlled homogeneity and/or heterogeneity of the material used to form the device by deposition methodologies, enhanced ability to control dimensional and mechanical characteristics of the device, the ability to fabricate complex device conformations, ability to pattern and control the porosity of the web and/or graft regions, and a monolithic one-piece construction of a device which yields a minimized device profile and cross-sectional area. The devices of the present invention have relatively thicker and thinner regions, in which the thinner regions permit radial collapse of the device for endoluminal delivery. The inventive device exhibits superior column strength that permits smaller introducer size and more readily facilitates deployment of the device.

FIGS. 6 and 7 depict the inventive web-stent and/or stent-graft, 40, 50. As illustrated in FIGS. 6 and 7, the web and/or graft regions, 44, 54 between adjacent structural members 42, 52 may be co-planar with either the luminal or abluminal surface of the structural members 42, or may be positioned intermediate the luminal 51 and abluminal 56 surfaces of the structural members 52.

In accordance with a preferred embodiment of the present invention, the web regions of the inventive web-stent, the graft regions of the inventive stent-graft and the inventive graft have a plurality of openings which pass through the thickness of the material used to fabricate the inventive devices. Each of the plurality of openings is dimensioned to permit cellular migration through the opening without permitting blood leakage or seepage through the plurality of openings. The plurality of openings may be random or may be patterned. However, in order to control the effective porosity of the device, it is desirable to impart a pattern of openings in the material used to fabricate the inventive device.

Figure 8C:
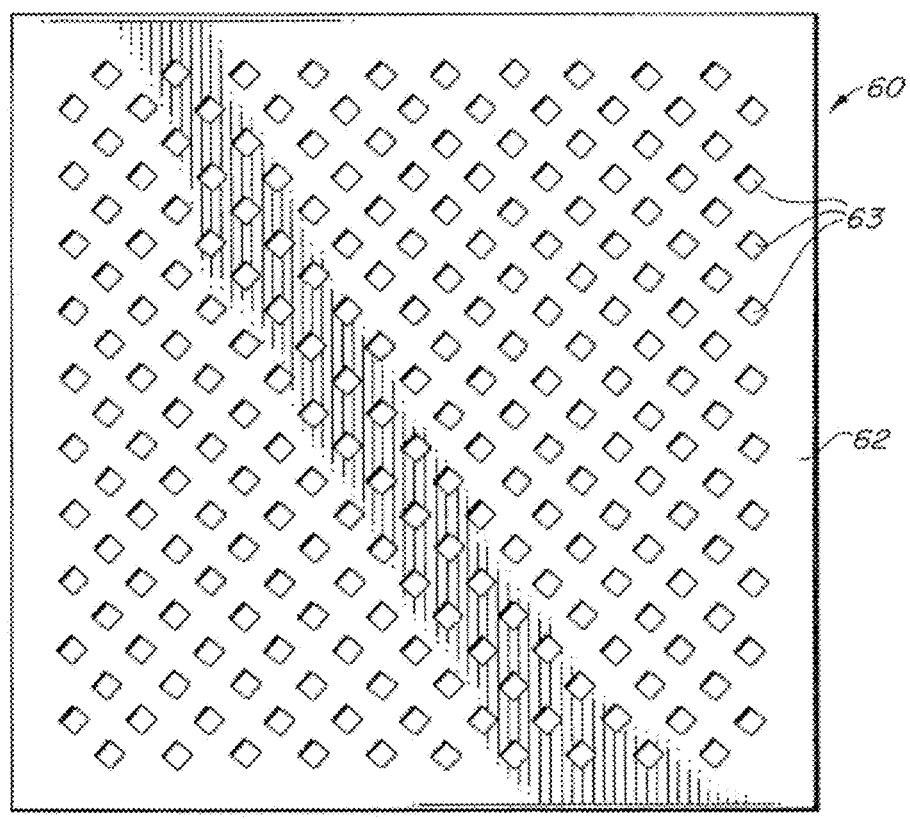

FIGS. 8A-8C depict several examples of patterned openings in a section of material used to make the inventive web-stent, graft regions of the stent-graft, and the inventive graft. FIG. 8A depicts a material 60 with a plurality of circular openings 64 passing through the material substrate 62. The plurality of circular openings is patterned in a regular array of rows and columns with regular inter-opening spacing 65 between adjacent openings. In the particular embodiment illustrated the diameter of each of the plurality of openings is about 19 µm, with an inter-opening spacing in each row and column of about 34 µm on center. The thickness of the material substrate 62 is approximately 10 µm. FIG. 8B illustrates another example of a pattern of a plurality of openings useful in the present invention. The material substrate 62, which again is approximately 10 µm in thickness, has a plurality of openings 66 and 67 passing there through. The pattern of the plurality of openings 66 and 67 is an alternating slot pattern in which the plurality of openings 66 are arrayed adjacent one and other forming a y-axis oriented array 68 relative to the material substrate 62, while a plurality of openings 67 are arrayed adjacent one and other forming an x-axis oriented array 69 relative to the material substrate 62. The y-axis-oriented array 68 and the x-axis-oriented array 69 are then positioned adjacent one and other in the material substrate 62. In this particular example, the inter-array spacing between the y-axis-oriented array 68 and the x-axis-oriented array 69 is about 17 µm, while each of the plurality of openings has a length of about 153 µm and a width of about 17 µm. Finally, FIG. 8C illustrates a material 60 in which the material substrate 62 has a regular array of a plurality of diamond-shaped openings 63 passing through the material substrate 62. As with the alternative embodiments exemplified in FIGS. 8A and 8B, the dimension of the plurality of diamond-shaped openings 63 is of sufficient size to permit cellular migration through the openings 63, while preventing blood flow or seepage through the plurality of openings 63.

FIGS. 9A and 9B illustrate alternate preferred embodiments of the graft 70 and graft 80 in accordance with the present invention. Graft 70 consists generally of concentrically positioned luminal graft member 74 and abluminal graft member 72 and an interfacial region 76 where the luminal surface of the abluminal graft member 72 and the abluminal surface of the luminal graft member 74 are in immediate juxtaposition with one and other. Both the luminal 74 and the abluminal 72 graft members are fabricated in accordance with the methodologies described above, and are provided with a plurality of patterned openings 73 in the abluminal graft member 72 and a plurality of patterned openings 75 in the luminal graft member 74. The plurality of patterned openings 73 and 75 are positioned out of phase relative to one another. By positioning the plurality of patterned openings 73 and 75 in an out-of-phase relationship, there is no continuous opening that passes through the interfacial region 76 which would permit blood flow or seepage from the lumen of the graft. However, in order to permit cellular migration from the abluminal surface of the graft to the lumen of the graft, the interfacial region 76 should have microroughness [not shown] which is oriented either randomly or selectively, such as helically or circumferential, about the interfacial region 76. The microroughness preferably has a peak-to-valley depth of between about 5µ to about 65µ, most preferably between about 10µ to 15µ, may be either on the luminal surface of the abluminal graft 72 or on the abluminal surface of the luminal graft 74, or both. The microroughness spans the surface area region between adjacent pairs of openings 73, 75, and the microroughness depth permits cellular migration across the surfaces between adjacent openings 73 and 75. The microroughness is not large enough to permit fluid passage through the inter-opening regions at the interface between the luminal graft 74 and the abluminal graft 72. This property of permitting cellular growth is similar to the difference between the porosity of expanded polytetrafluoroethylene grafts which do not require pre-clotting, and the much larger porosity of polyester or DACRON grafts which require pre-clotting to prevent fluid seepage there from.

FIG. 9B illustrates an alternative embodiment of the inventive graft 80 in which an abluminal graft member 82 is concentrically positioned about a luminal graft member 84. Each of the abluminal graft member 82 and the luminal graft member 84 having a plurality of patterned openings 83, 85, respectively, passing there through. As with the embodiment depicted in FIG. 9A, the plurality of patterned openings 83 and 85 are positioned in an out-of-phase relationship to one and other in order to prevent forming a continuous opening between the luminal and abluminal surfaces of the graft 80. However, unlike the embodiment in FIG. 9A, there is no corresponding interfacial region 76. Rather, an annular open region 87 is positioned intermediate the luminal graft member 84 and the abluminal graft member 82. The annular open region 87 is created by providing a plurality of microprojections 86 that project either radially inward from the luminal surface of the abluminal graft member 82 or radially outward from the abluminal surface of the luminal graft member 84. The plurality of microprojections 86 act as spacers which abut the opposing surface of either the luminal graft member 84 or the abluminal graft member 82 which bound the annular open region 87. The height of the microprojections 86 and, therefore, the size of the annular open region 87, are dimensioned such that cells may migrate through the annular open region 87, while blood flow or seepage will not occur between the lumen and the abluminal surface of the graft 80.

According to a specific aspect of the graft embodiment of the present invention, the size of the plurality of openings in the luminal graft member 74, 84 may be different than the size of the plurality of openings in the abluminal graft member 72, 82. For example, the plurality of openings in the abluminal graft member 72, 82 preferably have a larger size than the plurality of openings in the luminal graft member 74, 84, while still retaining the out-of-phase relationship between the plurality of openings in the luminal 74, 84 and the abluminal 72, 82 graft members. Where circular openings are provided, it is preferable that the luminal 74, 84 and the abluminal 72, 82 graft members have openings having diameters of between about 5 μm and 100 μm.

Additionally, a third member may be interposed between the luminal 74, 84 and the abluminal 72, 82 graft members. The third member will preferably have a very fine plurality of openings, such as on the order of between 2-10μ, and permits use of a higher porosity in the luminal and abluminal grafts, without the need to maintain an out-of-phase relationship between the openings in the luminal 74, 84 and the abluminal 72, 82 graft members.

Finally, the method 90 for fabricating the inventive grafts, stent-grafts and web-stents of the invention is illustrated in the process flow diagram in FIG. 10. As previously discussed above, a starting blank of material may be formed either by providing a pre-fabricated material blank of a biocompatible metal or metal-like material 92 or by vacuum depositing a starting blank of a biocompatible metal or metal like material film 94. Then a determination is made whether to employ an additive or a subtractive method 96 for forming the graft, stent-graft or web-stent. If an additive method is selected 97, the structural supports are built upon the starting blank 100, either by vacuum deposition techniques or by conventional metal forming techniques. If a subtractive method is selected 95, the regions to remain are masked 98, then the unmasked regions are removed, such as by chemical etching or sputtering, to form the interstitial web regions, graft regions and/or openings in either the interstitial web regions and/or graft regions 99.

The following examples are provided in order to illustrate the alternative embodiments of the invention, and are not intended to limit the scope of the invention.

Example 1

Stent Formation By Sputtering

A ceramic cylindrical substrate is introduced into a deposition chamber with capabilities of glow discharge substrate cleaning and sputter deposition of carbon and stainless steel. The deposition chamber is evacuated to a pressure less than or equal to $2\times10^{-7}$ Torr. Pre-cleaning of the substrate is conducted under vacuum by glow discharge. The substrate temperature is controlled to achieve a temperature between about 300 and 1100 degrees Centigrade. A bias voltage between −1000 and +1000 volts is applied to the substrate sufficient to cause energetic species arriving at the surface of the substrate to have hyperthermal energy between 0.1 eV and about 700 eV, preferably between 5-50 eV. The deposition sources are circumferential and are oriented to deposit from the target circumferentially about the substrate.

During deposition, the deposition pressure is maintained between 0.1 and 10 mTorr. A sacrificial carbon layer of substantially uniform thickness (5%) between 10 and 500 Angstroms is deposited circumferentially on the substrate. After depositing the carbon layer, a cylindrical film of stainless steel is deposited onto the sacrificial carbon layer on the cylindrical substrate at a deposition rate between about 10 to 100 microns/hour. After formation of the stainless steel film, the substrate is removed from the deposition chamber and heated to volatilize the intermediate sacrificial carbon layer between the substrate and the film. After removing the carbon intermediate layer, the stainless steel film is removed from the substrate and exhibits material properties similar to the bulk stainless steel target and surface properties characterized by controlled heterogeneities in grain size, material composition and surface topography. A series of patterns are then machined into the resultant stainless steel film to form a stent by electrical discharge machining (EDM) or laser cutting the film.

Example 2

Stent Formation by Sputtering

The same operating conditions are followed as in Example 1, except that the substrate is tubular and selected to have a coefficient of thermal expansion different than that of the resultant stent. No intermediate layer of sacrificial carbon is deposited onto the substrate, and the outer surface of the substrate is etched with a pattern of recesses defining a desired stent pattern. The substrate is mounted onto a rotational jig within the deposition chamber and rotated at a uniform rate during deposition. Tantalum is used as the target material and deposited into the recesses of the substrate from a single stationary source. After deposition, the temperature of the substrate and the deposited stent are controlled to impart diametric differential in the substrate and stent and permit removal of the stent from the substrate.

Example 3

Stent Formation by Ion Beam-Assisted Evaporative Deposition

A cylindrical substrate is introduced into a deposition chamber that has capabilities of: substrate rotation and precise positioning, glow discharge substrate cleaning, ion beam-assisted evaporative deposition, and cylindrical magnetron sputtering. The deposition sources are (a) dual electron beam evaporative sources placed adjacent to one another at the base of the deposition chamber at a fixed distance from the substrate, these are used with simultaneous argon ion impingement onto the substrate from a controlled ion beam source, and (b) a cylindrical magnetron sputtering source with a carbon target capable of circumferentially coating a carbon sacrificial layer of substantially uniform thickness of between 10 and 200 Angstroms onto the substrate.

The substrate temperature is controlled to achieve a substrate temperature between about 300 and 1100 degrees Centigrade. The deposition chamber is evacuated to a pressure less than or equal to $2\times10^{-7}$ Torr. A pre-cleaning of the substrate is conducted under vacuum by glow discharge. The substrate is rotated to ensure uniform cleaning and subsequent uniform deposition thickness. After cleaning the substrate is moved into the magnetron and coated with the carbon layer. The substrate is then moved into position to receive the stent-forming metal coating with simultaneous ion bombardment. One electron beam evaporation source contains titanium while the other source contains nickel. The evaporation rates of each of the titanium and nickel evaporation sources are separately controlled to form a nitinol alloy on the substrate as the stent-forming metal.

Example 4

Planar Deposition of Stent

The same operating conditions of Example 3 are followed, except that a planar substrate is used. The deposition source is a single electron beam evaporation source containing platinum and is used with simultaneous argon ion impingement onto the substrate from a controlled ion beam source.

The substrate temperature is controlled to achieve a substrate temperature between about 300 and 1100 degrees Centigrade. The deposition chamber is evacuated to a pressure less than or equal to $2\times10^{-7}$ Torr. A pre-cleaning of the substrate is conducted under vacuum by glow discharge. After cleaning the substrate is moved into position within the deposition chamber and coated with platinum from the electron beam evaporation source with simultaneous argon ion bombardment, with the electron beam evaporation source passing platinum through a pattern mask corresponding to a stent pattern which is interposed between the source and the substrate to pass a pattern of platinum onto the substrate.

After deposition, the patterned stent is removed from the substrate and rolled about a forming substrate to a cylindrical shape and opposing ends of the planar stent material are brought into juxtaposition with one another and may be attached by laser welding or left uncoupled.

Example 5

Thin-Film Deposition with Stent-Graft Etch

The same conditions are employed as in Example 4, except that a uniform layer of stent-forming material is deposited having a thickness of 150 microns without patterning of the stent onto the deposited layer. Rather, a negative mask is applied to the deposited stent-forming material, and a chemical etchant is introduced to etch a pattern of structural elements into the stent-forming metal. The etchant is permitted to react with the metal until a thinner film web having a thickness of between 2-75 microns, is present between adjacent structural elements. After the thinner film web is formed, the etching is stopped, and the resultant stent-graft is removed and formed into a tubular shape.

Example 6

Dry Etching Method

The same conditions as in Example 5 are followed, except that reactive ion etching is employed to form the thinner film web.

Example 7

Stent-Graft Formation

The same conditions are followed as in Example 5, except that the structural elements are defined in an intermediate region of a tubular substrate, and interstitial regions between adjacent structural elements are etched by chemical etching until interstitial openings are formed between adjacent structural elements while masking the structural elements and proximal and distal regions of the tubular substrate. Proximal and distal graft regions are formed adjacent the intermediate region of the tubular substrate and contiguous with the plurality of structural elements, by masking the structural elements and interstitial openings and chemical etching the proximal and distal regions of the tubular substrate to yield a thinner film of material in the proximal and distal regions of the tubular substrate. The proximal and distal graft regions are then everted, with the proximal graft region being inverted luminally through the lumen of the structural members and the distal graft region being everted abluminally over the structural members. The proximal graft region is mechanically joined to the distal terminal end of the plurality of structural members, while the distal graft region is mechanically joined to the proximal terminal end of the plurality of structural members, thereby encapsulating the plurality of structural members between the everted proximal and distal graft regions.

Example 8

Stent-Graft Formation—Discrete Graft and Discrete Stent

A pre-fabricated self-expanding superelastic shape memory alloy stent is provided. Two cylindrical hypotubes of a superelastic shape memory material similar to that of the stent are chemically etched to a substantially uniform thickness of 10 □m, with a first hypotube having an inner diameter which is of sufficient size to accommodate the outer diameter of the stent, and a second hypotube having an outer diameter dimensioned to accommodate the inner diameter of the stent. The etched hypotubes are then placed into a vacuum chamber and a cylindrical pattern mask having a regular array of circular openings, each circular opening having a diameter of about 25 µm, is positioned concentrically about each of the cylindrical hypotubes. The etched hypotubes are reactive ion etched to transfer the masked pattern to the etched hypotube and impart a pattern of circular openings that pass through the wall thickness of the etched hypotubes corresponding to the mask pattern. The stent, and first and second etched and reactive ion etched hypotubes are concentrically engaged upon one and other, with the second hypotube being concentrically positioned within the lumen of the stent and the first hypotube being concentrically positioned about the abluminal surface of the stent. Proximal and distal ends of the stent, the first hypotube and the second hypotube are mechanically joined by welding and then trimmed by laser cutting to ensure that the proximal and distal ends are co-terminus.

Example 9

Graft Formation

A cylindrical mandrel is provided which is coated with a sacrificial layer. A plurality of patterned recesses is defined in the sacrificial layer. The mandrel is introduced into a deposition chamber and a nickel-titanium alloy is vacuum deposited onto the mandrel, while rotating the mandrel, until a uniform adherent layer of the deposited nickel-titanium alloy covers the cylindrical mandrel. After deposition, the sacrificial layer is removed, and the uniform adherent layer disengaged from the cylindrical mandrel, yielding the inventive graft, with openings corresponding to the plurality of patterned recesses in the graft material.

While the invention has been described with reference to its preferred embodiments, those of ordinary skill in the relevant arts will understand and appreciate that the present invention is not limited to the recited preferred embodiments, but that various modifications in material selection, deposition methodology, manner of controlling the material heterogeneities of the deposited stent material, and deposition process parameters may be employed without departing from the invention, which is to be limited only by the claims appended hereto.

What is claimed is:

1. A method of fabricating an implantable medical device for supporting a physiological vessel, comprising the steps of:
   a. depositing an initial thin-film of biocompatible metal or metal-like material exhibiting at least one shape memory or superelastic property;
   b. forming from the initial thin-film a plurality of thin-film regions and a plurality of structural support regions bounding the thin-film regions, wherein the thin-film regions have a thickness different from a thickness of the structural support regions and at least one thin-film region is entirely terminally bounded by structural support regions; and
   c. etching a plurality of patterned microporous openings passing transversely through, in the thin-film regions.

2. The method of fabricating an implantable medical device according to claim 1, wherein the initial thin-film of biocompatible metal is fabricated of nitinol.

3. The implantable medical device according to claim 1, wherein the plurality of thin-film regions and the plurality of structural support regions are both fabricated of nitinol.

4. The method of fabricating an implantable medical device according to claim 1, wherein the plurality of structural support regions and the plurality of thin-film regions are fabricated of at least one of a metal or metal-like material exhibiting at least one shape memory or superelastic property.

5. The method of fabricating an implantable medical device according to claim 4, wherein the plurality of structural support regions and plurality of thin-film regions are fabricated of nitinol.

6. The method of fabricating an implantable medical device according to claim 1, wherein the plurality of patterned microporous openings each have a maximum dimension sufficient to permit cellular migration there through without permitting fluid flow there through.

7. The method of fabricating an implantable medical device according to claim 1, wherein each of the plurality of patterned microporous openings have a maximum dimension of about 19 μm.

8. The method of fabricating an implantable medical device according to claim 1, wherein the plurality of structural support regions comprises struts.

9. The method of claim 1, wherein the forming step of the plurality of thin-film regions and the plurality of structural support regions bounding the thin-film regions further comprises etching.

10. The method of claim 1, wherein the forming step of the plurality of thin-film regions and a plurality of structural support regions bounding the thin-film regions further comprises a step of forming a tubular member having a plurality of thin-film regions and a plurality of structural support regions bounding the thin-film regions.

11. The method of claim 1, further comprising depositing a graft member over the plurality of patterned microporous openings.

12. The method of claim 1, further comprising depositing a graft member over the plurality of structural support regions and attaching the graft member to opposing ends of the thin film.

* * * * *